United States Patent
Shim et al.

(10) Patent No.: US 11,052,098 B2
(45) Date of Patent: Jul. 6, 2021

(54) COMPOSITION CONTAINING ARALOSIDE FOR EXTERNAL APPLICATION TO SKIN

(71) Applicant: Amorepacific Corporation, Seoul (KR)

(72) Inventors: Jin Sup Shim, Yongin-si (KR); Jae Young Ko, Yongin-si (KR); Mi Suk Yang, Yongin-si (KR); Se Jin Yoo, Yongin-si (KR); Ho Hyun Song, Yongin-si (KR); Yong Jin Kim, Yongin-si (KR); Jon Hwan Lee, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 416 days.

(21) Appl. No.: 15/779,749

(22) PCT Filed: Nov. 30, 2016

(86) PCT No.: PCT/KR2016/013985
§ 371 (c)(1),
(2) Date: May 29, 2018

(87) PCT Pub. No.: WO2017/095146
PCT Pub. Date: Jun. 8, 2017

(65) Prior Publication Data
US 2020/0306278 A1    Oct. 1, 2020

(30) Foreign Application Priority Data
Nov. 30, 2015   (KR) .................. 10-2015-0169139

(51) Int. Cl.
| | | |
|---|---|---|
| A61K 31/704 | (2006.01) | |
| A61K 8/60 | (2006.01) | |
| A61K 9/00 | (2006.01) | |
| A61Q 19/08 | (2006.01) | |
| A61K 9/06 | (2006.01) | |

(52) U.S. Cl.
CPC .............. *A61K 31/704* (2013.01); *A61K 8/60* (2013.01); *A61K 9/0014* (2013.01); *A61Q 19/08* (2013.01); *A61K 9/06* (2013.01)

(58) Field of Classification Search
CPC ....... A61K 31/704; A61K 8/60; A61K 9/0014
See application file for complete search history.

(56) References Cited

U.S. PATENT DOCUMENTS

2003/0104079 A1*   6/2003   Sakanaka ............. A61K 31/704
424/728

FOREIGN PATENT DOCUMENTS

| CN | 1552723 A | 12/2004 |
|---|---|---|
| JP | 2010241779 A | 10/2010 |
| KR | 10-2005-0071275 A | 7/2005 |
| KR | 10-2006-0131016 A | 12/2006 |
| KR | 10-0829045 B1 | 5/2008 |
| KR | 10-2010-0081627 A | 7/2010 |
| KR | 10-2013-0035325 A | 4/2013 |
| KR | 10-1415996 B1 | 7/2014 |

OTHER PUBLICATIONS

PubChem (https://pubchem.ncbi.nlm.nih.gov/compound/Araloside-A; downloaded on Nov. 10, 2020).*
Kanako (Planta Med; 2006, 72; 193-198).*
International Search Report for PCT/KR2016/013985 dated Mar. 6, 2017.
Zhang Jia-xin et al., "Research progress in chemical constituents of saponins from Aralia elata and their pharmacological activities", Chinese Traditional and Herbal Drugs, 2013, 44(6): 770-779 ( 11 pages total).
Zhou Chong-Chu et al., "Effect of aralosides on allergic reaction", Chinese Journal of Pharmacology and Toxicology, 1991, 5(1), pp. 34-37(5 pages total).
Li Ming et al., "Pharmacological Research Progress of Aralia Elata", Medical Recapitulate, vol. 15, No. 2, pp. 3157-3160 (5 Pages Total), abstract is considered.
Communication dated Oct. 28, 2020 by the National Intellectual Property Administration of the People's Republic of China in application No. 201680069827.5.

* cited by examiner

*Primary Examiner* — Pancham Bakshi
(74) *Attorney, Agent, or Firm* — Sughrue Mion, PLLC

(57) ABSTRACT

The present invention relates to a composition comprising an araloside-based compound and, more particularly, to a composition for external application to skin, the composition comprising, as an active component, an araloside-based compound, including araloside X, araloside V and araloside VII. Thus, the composition restores skin markers damaged by external environmental stress, such as harmful substances or fine dusts, and reduces the expression of skin inflammatory factors to help the recovery of damaged skin, thereby providing effects, such as anti-oxidation, skin trouble suppression, anti-inflammation, or skin barrier improvement.

3 Claims, 1 Drawing Sheet

【FIG. 1】
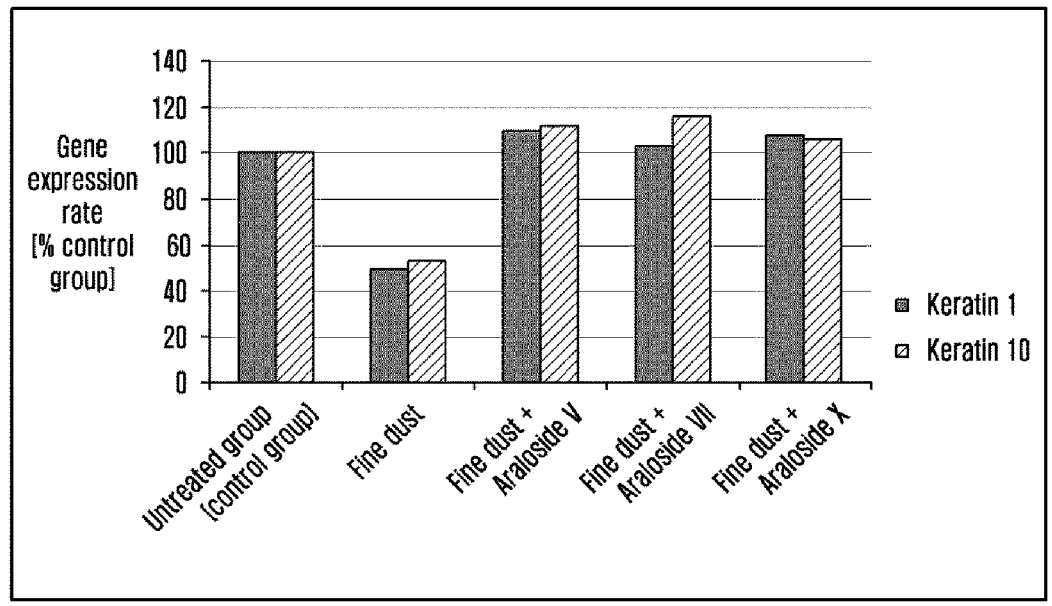
【FIG. 2】
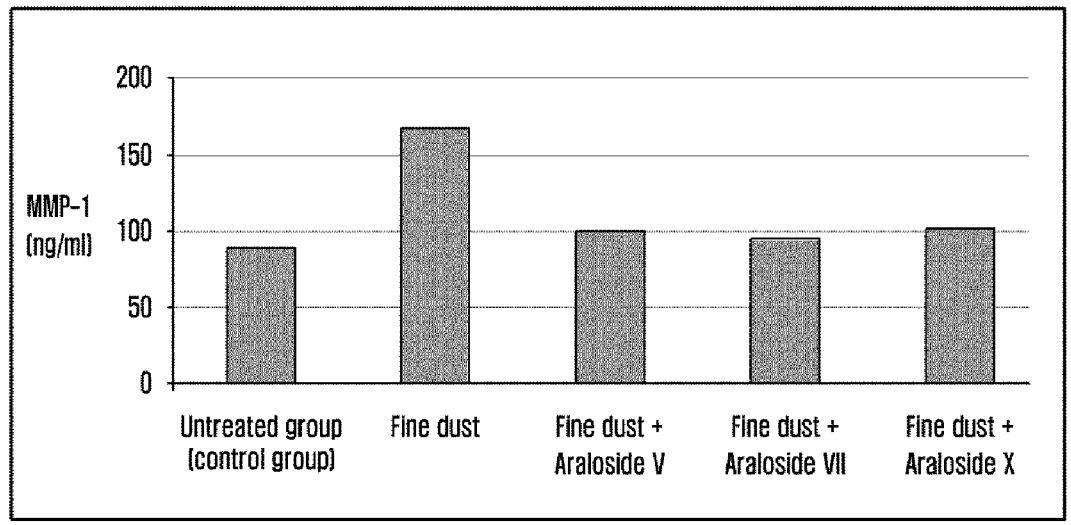

COMPOSITION CONTAINING ARALOSIDE FOR EXTERNAL APPLICATION TO SKIN

CROSS REFERENCE TO RELATED APPLICATIONS

This application is a National Stage of International Application No. PCT/KR2016/013985 filed Nov. 30, 2016, claiming priority based on Korean Patent Application No. 10-2015-0169139 filed Nov. 30, 2015.

TECHNICAL FIELD

The present invention relates to a composition comprising an araloside-based compound and, more particularly, to a composition for external application to skin, comprising, as an active component, an araloside-based compound, including araloside X, araloside V and araloside VII, and thus, the composition restores skin markers damaged by external environmental stress, such as harmful substances or fine dusts, reduces the expression of skin inflammatory factors to help the recovery of damaged skin, thereby providing beneficial effects, such as anti-oxidation, skin trouble suppression, anti-inflammation, or skin barrier improvement.

BACKGROUND ART

In urban areas and industrial complexes, automobile exhaust gas, yellow sands or external pollutants, including fine heavy metal dusts, flying through industrial zone eastern can contaminate people's skin and cause skin aging and skin, troubles. This is mainly due to heavy metals and fine dusts contained in the pollutants.

The heavy metals refers to all metals having a specific gravity of 4 or more such as mercury, cadmium, lead and copper. Generally, when heavy metals are absorbed in a living body, they combine with substances in the living body to form organic complexes which are not well decomposed. Therefore, the heavy metals are potent substances that are not discharged quickly to the outside of the body, but accumulated in organs such liver, kidney, and bones. When exposed to a small amount or heavy metal for a long period of time, it is likely to cause symptoms such as hind leg paralysis, abnormal movement, ataxia, skin pigmentation or keratinization, atrophic defect of nail or hoof and hair, reproductive dysfunction, malformation birth, decline growth and reduction in immune function. In the skin, these harmful heavy metals and fine dusts cause a chemical reaction in the atmosphere to additionally generate harmful substances such as nitrogen oxides (NO), sulfur oxides (SO), and the like, thereby increasing cytokines or the like which are skin inflammatory substances, or causing atopy or skin troubles. In addition, it is already known that heavy metals destroy hyaluronic acid, which is closely related to skin moisturization.

Since the fine dusts have usually a size of 10 μm or less and the heavy metal particles have a size of 2 μm or less, they have much smaller sizes than general dusts (average size of 20 μm or more).

According to research results by the National Institute of Environmental Research (2006), fine dusts in the Seoul metropolitan area were found to be mainly composed of sulphates, nitrates produced from automobile exhaust gas, and secondary products flew from China (Fine dust (PM10) in Jeonnong-dong, Seoul City showed 22% of organic carbon compounds, 8% of elemental carbon, 22% of nitrates, 15% of sulfates, 15% of components of soil crusts and 18% of other components. Source: National Institute of Environmental Research in 2006). Since fine dusts permeate deeply into the human alveolus and accumulate in the bronchi and lungs, they may cause directly various respiratory diseases, decrease the body's immune function, cause asthma and dyspnea, and increase the concentration of heavy metals in rain or snow due to long-distance movement. In the skin, since size fine of dusts is small, they can easily penetrate deeply into the pores. If penetrated fine dusts are not cleanly removed, skin inflammation and troubles often occur.

Current methods for removing heavy metals in the body include a method of injecting a complex-forming substance such as EDTA (ethylene diamine tetraacetate) and BAL (British anti-Lewisite) and a lowing it to bind with heavy metals accumulated in the body so that heavy metals are discharged from the body, or a method of taking vitamin B1, vitamin C and vitamin to prevent the absorption of heavy metals the body and to facilitate the discharge. However, there is no way to actually remove heavy metals accumulated on the surface of the skin effectively and easily. Fine dust can be removed to some extent by cleansing, but as it is finer, the adsorption force is stronger. Therefore, it is impossible to completely remove fine dust deeply penetrated into the pores, particularly, ultrafine dust having a diameter of 2.5 μm or less by general cleansing. There is a need for a means that can regulate inflammatory factors capable of inducing skin troubles and can recover skin markers damaged by external environmental stress.

On the other hand, the skin is a body part that is directly exposed to the external environment. When the skin is exposed to external environmental stress such as excessive ultraviolet rays and pollutants, skin irritation such as erythema, edema, itching and inflammation is induced. It is known that skin troubles due to such stress not only cause aesthetic problems but also allow substances produced in the course of the inflammatory reaction to incidentally cause pigmentation of the skin and promote the disintegration of the elastic fibers of the skin, thereby affecting the increase of skin wrinkles.

Therefore, in order to reduce skin irritation and inflammation due to various stresses, and to reduce skin site effects resulting from the use of cosmetic products and percutaneous absorption drug systems, there is a desperate need to develop a substance having a skin irritation-mitigating effect.

PRIOR ART LITERATURE

Patent Literature

1. Korean Patent No. 10-1415996 (published on Jul. 8, 2014)

DETAILED DESCRIPTION OF THE INVENTION

Technical Problem

Thus, the present inventors have attempted to find out a substance that can recover skin markers (for example, keratin 1, keratin 10, etc.) which are damaged by harmful substances or ultrafine dusts or exhibit inhibited expression, and that can normalize damaged skin by inhibiting the activity of markers (for example, IL8, IL1B) involved in an inflammatory reaction with an increase in the activity. As a result, the inventors have found that araloside can provide these effects, thereby completing the present invention.

Therefore, an object of the present invention is to provide a composition for external application to skin, comprising an araloside as an active component, the composition capable of normalizing damaged skin markers, inhibiting the activity of the inflammation-inducing factor to exert a skin irritation-mitigating effect, and thus exhibiting effects such as anti-oxidation, skin trouble suppression, anti-inflammation, or skin barrier improvement.

Technical Solution

In order to achieve the above objects, the present invention provides a skin preparation composition for external use, e.g., for skin irritation-mitigation, anti-oxidation, anti-aging, skin trouble suppression, and anti-inflammation, comprising an araloside as an active component.

The present invention also provides the use of an araloside-based compound as an antioxidant, as a skin trouble-suppressing agent, as an inflammation-mitigating agent, or as a skin cell damage-preventing agent in the production of a composition for external application to skin (specifically, a cosmetic composition or a pharmaceutical composition).

In addition, the present invention provides the use of an araloside-based compound as a therapeutic agent for inflammatory skin diseases in the production of a pharmaceutical composition.

Advantageous Effects

The composition of the present invention comprises an araloside, and thus restores skin markers damaged by external environmental stress, such as harmful substances or fine dusts like ultrafine dusts to alleviate skin irritation, and reduces the expression of skin inflammatory factors to help the recovery of damaged skin, thereby providing effects, such as anti-oxidation, skin trouble suppression, anti-inflammation, or skin barrier improvement.

BRIEF DESCRIPTION OF DRAWINGS

FIG. 1 is a graph showing the extent of activity recovery level of keratin 1, keratin 10 marker by aralosides V, VII, and X in cells treated with fine dust.

FIG. 2 is a graph showing the extent of inhibition of MMP-1 by aralosides V, VII, and X in cells treated with fine dust.

DETAILED DESCRIPTION OF THE EMBODIMENTS

The present invention provides a composition for external application to skin, comprising an araloside-based compound.

The araloside-based compound used as an active component in the present invention is a saponin glycoside. When araloside is hydrolyzed, components as oleanolic acid, arabinose, glucose, glucuronic acid, choline and alkaloid are extracted. Since these components act to excite the central nervous system, it is known that the araloside is effective for treating nervous breakdown, schizophrenia, headache and hypotension and that it is also used for gastric ulcers and stomach cancers.

The araloside-based compound can be specifically divided into sub-classes: aralosides A, B, C, V, VII, and the like. Preferably, in the present invention, the araloside VII or X is used as an active component, and the specific structures thereof are as shown in the following Chemical Formulas 1 to 3.

[Chemical Formula 1]

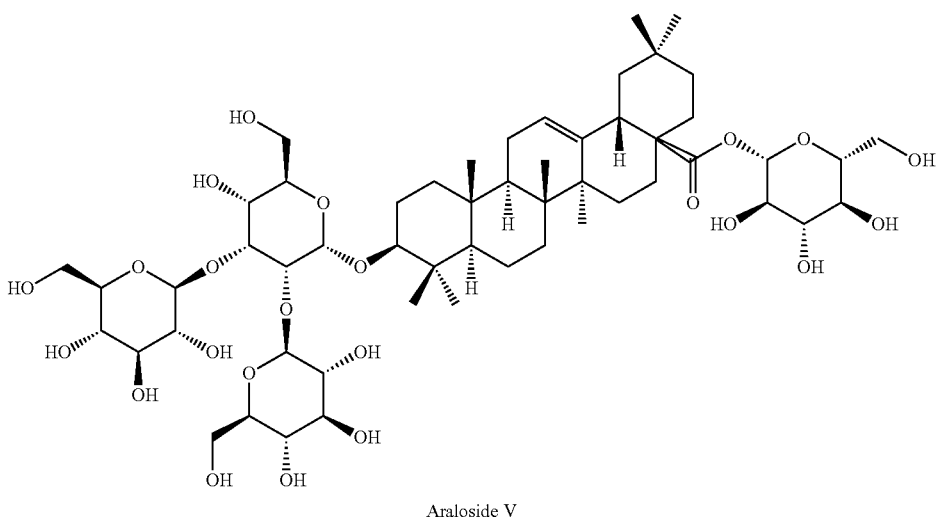

Araloside V

-continued

[Chemical Formula 2]

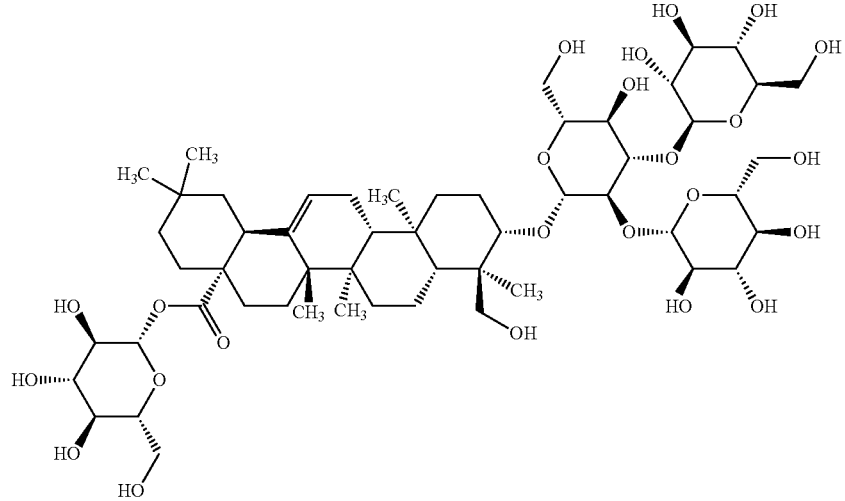

Araloside VII

[Chemical Formula 3]

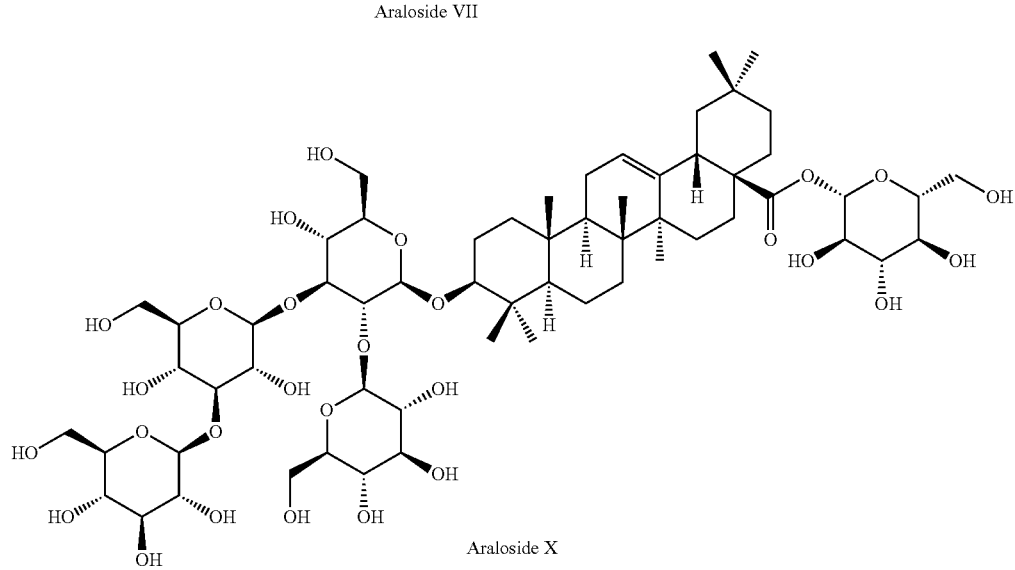

Araloside X

Araloside used in the present invention commercial available or can be obtained according to a conventional method in the art, and the production method thereof is not particularly limited. As a specific example, the araloside used in the present invention is available from Chengdu Biopurify Phytochemicals LTD. (China).

The composition of the present invention may contain an araloside in an amount of 0.0001 to 30% by weight based on the total weight of the composition. In particular, individual aralosides can be contained in an amount of 0.0001 to 10% by weight, respectively. When the content is less than 0.0001% by weight, it difficult to expect the proper skin absorption, stability and desired effects of the component. When the content exceeds 10% by weight, it may adversely affect the safety and stability of the product.

The composition according to the present invention comprises, as an active component, an araloside, particularly at least one araloside selected from the group consisting of araloside V, araloside VII and araloside X, and thus it can help to restore skin damage caused by external environmental stress and to alleviate skin irritation.

As used herein, the term "external environmental stress" means a factor including external harmful substances, fine dusts, and the like which can irritate a skin.

As used herein, the term "skin irritation" means that the skin condition is not at a normal level, and includes, for example, conditions such as skin dryness, inflammation, erythema, keratin, itching or burning.

As used herein, the term "harmful substance" means a substance that can irritate a skin to cause skin damage. In the present invention, it is particularly intended to include heavy metals.

As used herein, the term "fine dust" is a very small substance that is not visible to the naked eye, and refers to a particulate matter with a diameter of 10 μm or less that floating or flying in the atmosphere for long periods of time. The dust is divided into fine dust having a diameter of 10 μm or less (PM10) and ultrafine dust having a diameter of 2.5 μm or less (PM2.5) depending on the particle size. In the present invention, the fine dust is also intended to include ultrafine dust.

As used herein, the term "inflammatory skin disease" refers to a skin disease that causes inflammation due to external or internal stress the skin, and refers to accompanying symptoms such as inflammation, erythema, keratin, itching or burning.

In the present invention, the interleukin-8 (IL8) and interleukin-1 beta (IL1B) are genes involved in an inflammatory reaction such as secretion of an inflammatory mediator (also referred to as "skin inflammation-inducing factor"), which are reported to be significantly induced due to fine dust and ultrafine dust. The use of the composition according to the present invention can inhibit the expression of the IL8 and IL1B genes, which are skin inflammation-inducing factors, or reduce the activity of proteins expressed by the genes.

In the present invention, the keratin 10 and keratin 1 are genes that have a function to normalize epidermal keratinization by regulating keratinization of skin cells, and they are involved in skin damage, erythema, skin wrinkles, aging and the like due to fine dust and ultrafine dust. The use of a composition according to the present invention can increase the expression of these keratin 1 and keratin 10 or increase the activity of the protein expressed by the gene.

The composition of the present invention uses an araloside as an active component, and thereby facilitate the discharge harmful substances and fine dusts, particularly ultrafine dust, adsorbed on the skin from the body, and allows skin markers, for example, marker genes such as keratin 1, keratin 10, etc., exhibiting damaged activity or inhibited expression due to harmful substances or fine dusts to restore to normal levels and so increase the expression of a gene or the activity of a protein expressed by the gene and decrease the expression of skin inflammation-inducing factor, for example, marker genes such as IL8, IL1B or the activity of a protein expressed by the gene to help skin recovery, and further provide excellent skin protection efficacy from external irritation. In addition, by controlling the expression of the marker gene or the activity of the protein expressed by the gene, it may act effectively for skin anti-aging, such as anti-oxidation, improvement of skin diseases, prevention or improvement of skin inflammation, improvement of skin barrier, improvement of skin wrinkling and increase of skin elasticity, and thus can help to normalize damaged skins.

The skin preparation composition for external use of the present invention can be formulated as a cosmetic composition, and can be formulated by incorporating a cosmetically or dermatologically acceptable medium base. The composition present invention can also be formulated in any dosage form suitable for topical application. For example, the composition can provided in the form of an oil-in-water type emulsion, a water-in-oil type emulsion, a suspension, a solid, a gel, a powder, a paste, a foam or an aerosol. Specifically, the composition of the present invention may be provided in the form of a cream, a skin, a lotion, a powder, an ointment, a spray or a conceal stick. Compositions of these dosage forms can be prepared by conventional methods in the art.

In addition to the above-mentioned substances, the composition according to the present invention may contain preferably other components which can impart a synergistic effect to the main effect, within a range that does not impair the main effect. Further, the composition according to the present invention may further comprise a moisturizing agent, an emollient agent, an ultraviolet absorber, a preservative, a bactericide, an antioxidant, a pH adjuster, an organic or inorganic pigment, a flavoring agent, a cold-feeling agent or a sweat restraint. The blending amount of the respective components can be easily selected by those skilled in the art within a range that does not impair the object and effect of the present invention. For example, the blending amount thereof may be 0.0001 to 10% by weight, specifically 0.001 to 5% by weight, more specifically 0.01 to 3% by weight based on the total weight of the composition.

The cosmetic composition of the present invention is not particularly limited in its formulation. For example, it can be formulated into cosmetic products such as skin softener, astringent lotion, nutrition lotion, nutritive cream, massage cream, essence, eye cream, eye essence, pack, powder, body lotion, body cream, body oil and body essence. In addition, the composition according to the present invention may be formulated as a cleaning composition. Specifically, it can be formulated into shampoo, rinse, hair treatment, body cleanser, soap, cleansing foam, cleansing water, cleansing cream, cleansing gel and the like.

The composition for external application to skin according to the present invention may be a pharmaceutical composition. The pharmaceutical composition may further comprise pharmaceutical adjuvants such as preservatives, stabilizers, wetting agents or emulsifying accelerators, salts and/or buffers for controlling an osmotic pressure, and other therapeutically useful substances. The pharmaceutical composition may be formulated into lotions, creams, ointments or gels and the like.

The pharmaceutical composition is preferably transdermally administered.

Hereinafter, the present invention will be described in more detail by way of examples. It will be obvious to those skilled in the art that these examples are provided for illustrative purposes only and that the scope of the present invention is not construed as being limited by these examples.

[Referential Example 1] Preparation of Araloside-Based Compound

To test the efficacy of the present invention, araloside V, araloside VII, and araloside X were purchased from Chengdu Biopurify Phytochemicals LTD. (China).

[Referential Example 2] Preparation of Fine Dust

To test the efficacy of the present invention, fine dust (PM10-like) was purchased from Sigma-Aldrich (USA). Thereafter, the fine dust was dispersed in sterilized physiological saline at a concentration 100 ppm before use, and then used within 24 hours.

[Test Example 1] Confirmation of Recovery Efficacy of Expression Levels of Keratin 1 and Keratin 10 Marker Genes Human neonatal epidermal keratinocytes (HEK; Lonza, NHEK-Neo-Neonatal Normal. Human Epidermal Keratinocytes, Pooled) were dispensed in medium (KBM-gold, Lonza) in a 6-well plate at a density of $1 \times 10^5$ cells per well and cultured at 37° C. for 24 hours. 100 ppm of fine dust was treated in the well and subjected to stimulation for 24 hours, which was then treated with medium (KBM-gold, Lonza) containing 50 ppm each of araloside araloside VII and araloside X and incubated at 37° C. for 5 days. Then, RNA was extracted from the HEK cells incubated for 5 days using an RNeasy mini kit (Qiagen), and then a cDNA was synthesized through an RT-PCR process using a Superscript III kit (Invitrogen). To confirm the expression level of keratin 1 and keratin 10 genes, a probe (TaqMan™ fluorogenic probe, Hs00196158_m1, Hs00166289_m1) was used to conduct the quantitative real-time PCR process and observe the expression behavior of keratin 1 and keratin. 10. The results were shown in FIG. 1. The control group used an untreated group not treated with fine dust and also not treated with araloside V, araloside VII and araloside X; and fine dust-treated group treated with fine dust but not, treated with araloside V, araloside VII and araloside X.

From the results in FIG. 1, it could be confirmed that araloside V, araloside VII and araloside X had an effect to recover the expression of keratin 1 and keratin 10 genes inhibited due to fine dust, compared to the group treated with only fine dust, thereby recovering the expression of keratin 1 and keratin 10 genes to a level equal to or higher than that in the untreated group (control group).

[Test Example 2] Confirmation of Expression Regulatory Effect of IL8 and IL1B Marker Genes Human fibroblasts (PromoCell, Germany) were inoculated in a 6-well plate at a concentration of $1 \times 10^5$ cells, and cultured in an incubator (37° C., 5% $CO_2$) for 24 hours. 100 ppm of fine dust was treated in the well and subjected to stimulation for 24 hours, which was then treated with medium containing 50 ppm each of araloside V, araloside VII and araloside X and allowed to react for 48 hours. After completion of the reaction, the culture solution was collected and subjected to ELISA analysis. At this time, α-bisabolol, a substance frequently used as an anti-inflammatory and irritation-mitigating agent, was used as a control group. Measurement of the production amount of IL8 and IL1B proteins was carried out using a ThermoFisher's kit, and experiments were conducted according to the method described in the company's manual. The measurement results are shown in Table 1 below.

TABLE 1

| Sample (50 ppm) | IL8 (pg/ml) | IL1B (pg/ml) |
|---|---|---|
| Fine dust (100 ppm) | 246 | 311 |
| Control (α-bisabolol) | 180 | 214 |
| Fine dust + araioside V | 189 | 243 |
| Fine dust + araioside VII | 184 | 256 |
| Fine Dust + araloside X | 187 | 252 |

From the result in Table 1, it could be confirmed that the production amount of IL8, IL1B proteins was remarkably decreased due to the addition of the components of aralosides V, VII or X used in the present invention, thereby showing a high inhibitory effect for the production of an inflammation-inducing factor.

[Test Example 3] Confirmation of MMP-1 Inhibitory Effect

Human neonatal fibroblast HS68 was purchased from Cascade Biologics (Invitrogen, USA) and used. Hs68 was cultured using DMEM medium supplemented with 10% FBS (fetal bovine serum), 50 U/ml of penacillin and 50 μg/ml of streptomycin. Cells were cultured under the conditions of 37° C., 5% $CO_2$. The Hs68 was added to a 12-well plate at a concentration of $7.5 \times 10^4$ cells/well and cultured overnight. On the next day, the medium was replaced with FBS-free medium having a fine dust concentration of 100 ppm and cultured for 24 hours. After irradiating with UVB 30 mJ/M², the araloside V, araloside VII, and araloside X were treated at a concentration of 50 ppm for 48 hours, respectively. After culture, the medium was collected and the production amount of MMP-1 was measured using an MMP-1 assay kit (GE healthcare). The results are shown in FIG. 2. The control group used an untreated group not treated with fine dust and also not treated with araloside V, araloside VII and araloside X; and a fine dust-treated group treated with fine dust but not treated with araloside V, araloside VII and araloside X.

From the results FIG. 2, it could be confirmed that, compared to the group treated with only fine dust, araloside V, araloside VII and araloside X inhibited MMP-1 activity significantly elevated due to fine dust, to about the level of MMP-1 activity in the untreated (control) group.

[Test Example 4] Inhibitory Effect on Reactive Oxygen Species (ROS) Production $5 \times 10^4$ Keratinocytes isolated from human epidermal tissue were added to each well of a 24-well plate and allowed to adhere for 24 hours. Then, araloside araloside VII and araloside X were treated at 50 ppm, respectively. At this time, for comparison, a control group (untreated group) was not treated with araloside V, araloside VII and araloside X, and a positive control group was treated with a known antioxidant ascorbic acid. After 2 hours, the culture solution was removed, and then 100 μl of phosphate buffered saline (PBS) containing 100 ppm of fine dust was added to each well. Then, the amount of active oxygen species increased by fine dust stimulation was quantified. The amount of ROS was quantified with reference to Tan's method of measuring the fluorescence of DCF-DA (dichlorofluorescin diacetate) oxidized by ROS (Tan et al., 1998, J. Cell Biol. Vol. 141, pp 1423-1432). The ratios of the control group treated with only vehicle to ROS were calculated, and the results are shown in Table 2 below.

TABLE 2

| Test material | Treated with 100 ppm of fine dust |
|---|---|
| Control group (vehicle) | 100 |
| Fine dust (100 ppm) | 384 |
| Fine dust + araloside V | 110 |
| Fine dust + araloside VII | 105 |
| Fine dust + araloside X | 102 |
| Fine dust + ascorbic acid (50 ppm) | 200 |

From the results in Table 2, it can be seen that araloside V, araloside VII, and araloside X used in the present invention effectively inhibit the production of ROS, which is known to cause damage of skin cells by fine dust, and also have an excellent antioxidant effect because the amount of ROS after treatment of fine dust is inhibited at a level higher than ascorbic acid which is known to have excellent antioxidant effect.

Therefore, it is confirmed that araloside V, araloside VII and araloside X according to the present invention can suppress oxidation by fine dust, prevent skin aging and thus prevent the pores from widening, and further they can improve skin trouble by protecting the generation of skin irritation.

[Formulation Example 1] Skin Lotion

Skin lotion is prepared using the composition described in Table 3 below according to a conventional method.

TABLE 3

| | Content (wt %) |
|---|---|
| At least one of araloside V, araloside VII and araloside X | 0.2 |
| Glycerin | 3.0 |
| Butylene glycol | 2.0 |
| Propylene glycol | 2.0 |
| Carboxyvinyl polymer | 0.1 |
| PEG 12 nonylphenyl ether | 0.2 |
| Polysorbate 80 | 0.4 |
| Ethanol | 10.0 |
| Triethanol amine | 0.1 |
| Preservative, pigment, flavoring agent | Adequate amount |
| Purified water | Residual amount |

[Formulation Example 2] Nutritive Cream

Nutritive cream was prepared using the composition described in Table 4 below according to conventional method.

TABLE 4

| | Content (wt %) |
|---|---|
| At least one of araloside V, araloside VII, and araloside X | 0.2 |
| Polysorbate 60 | 1.5 |
| Sorbitan sesquioleate | 0.5 |
| PEG 60 hardened castor oil | 2.0 |
| Liquid paraffin | 10.0 |
| Squalane | 5.0 |
| Caprylic/capric triglyceride | 5.0 |
| Glycerin | 5.0 |
| Butylene glycol | 3.0 |
| Propylene glycol | 3.0 |
| Triethanol amine | 0.2 |
| Preservative, pigment, flavoring agent | Adequate amount |
| Purified water | Residual amount |

[Formulation Example 3] Massage Cream

Massage cream was prepared using the composition described in Table 7 below according to a conventional method.

TABLE 5

| | Content (wt %) |
|---|---|
| At least one of araloside V, araloside VII and araloside X | 0.1 |
| Bees wax | 10.0 |
| Polysorbate 60 | 1.5 |
| PEG 60 hardened castor oil | 2.0 |
| Sorbitan sesquioleate | 0.8 |
| Liquid paraffin | 40.0 |
| Squalane | 5.0 |
| Caprylic/capric triglyceride | 4.0 |
| Glycerin | 5.0 |
| Butylene glycol | 3.0 |

TABLE 5-continued

| | Content (wt %) |
|---|---|
| Propylene glycol | 3.0 |
| Triethanol amine | 0.2 |
| Preservative, pigment, flavoring agent | Adequate amount |
| Purified water | Residual amount |

[Formulation Example 4] Pack

Pack was prepared using the composition described in Table 6 according to a conventional method.

TABLE 6

| | Content (wt %) |
|---|---|
| At least one of araloside V, araloside VII and araloside X | 1.0 |
| Polyvinyl alcohol | 13.0 |
| Sodium carboxymethyl cellulose | 0.2 |
| Glycerin | 5.0 |
| Allantoin | 0.1 |
| Ethanol | 6.0 |
| PEG 12 nonylphenyl ether | 0.3 |
| Polysorbate 60 | 0.3 |
| Preservative, pigment, flavoring agent | Adequate amount |
| Purified water | Residual amount |

[Formulation Example 5] Gel

Gel was prepared using the composition described in Table 7 below according to a conventional method.

TABLE 7

| | Content (wt %) |
|---|---|
| At least one of araloside V, araloside VII and araloside X | 0.05 |
| Ethylene diamine sodium acetate | 0.05 |
| Glycerin | 5.0 |
| Carboxy vinyl polymer | 0.3 |
| Ethanol | 5.0 |
| PEG 60 hardened castor oil | 0.5 |
| Triethanol amine | 0.3 |
| Preservative, pigment, flavoring agent | Adequate amount |
| Purified water | Residual amount |

[Formulation Example 6] Ointment

Ointment was prepared using the composition described in Table 8 below according to a conventional method.

TABLE 8

| | Content (wt %) |
|---|---|
| At least one of araloside V, araioside VII and araloside X | 0.1 |
| Glycerin | 8.0 |
| Butylene glycol | 4.0 |
| Liquid paraffin | 15.0 |
| Beta glucan | 7.0 |
| Carbomer | 0.1 |
| Caprylic/capric triglyceride | 3.0 |
| Squalane | 1.0 |
| Cetearyl glucoside | 1.5 |
| Sorbitan stearate | 0.4 |
| Cetearyl glucoside | 1.0 |
| Bees wax | 4.0 |
| Preservative, pigment, flavoring agent | Adequate amount |
| Purified water | Residual amount |

Although specific parts of the present invention have been described in detail, it will be apparent to those skilled in the art that these specific techniques are merely a preferred embodiment and that the scope of the present invention is not limited thereto. Therefore, the substantial scope of the present invention will be defined by the accompanying claims and their equivalents.

The invention claimed is:

1. A method for reducing skin inflammation, comprising administering an effective amount of a composition comprising, as an active ingredient, an isolated araloside-based compound to skin with inflammation,
   wherein the isolated araloside-based compound is one or more selected from the group consisting of araloside V, araloside VII, and araloside X.

2. The method according to claim 1, wherein the reducing skin inflammation comprises preventing skin cell damage.

3. The method according to claim 1, wherein the reducing skin inflammation comprises suppressing a skin trouble.

* * * * *